United States Patent [19]

Loev et al.

[11] Patent Number: 4,500,528
[45] Date of Patent: Feb. 19, 1985

[54] N-SUBSTITUTED 1,4-DIHYDROPYRIDINES AND PHARMACEUTICAL COMPOSITIONS

[75] Inventors: Bernard Loev, Scarsdale; Howard Jones, Ossining, both of N.Y.; James R. Shroff, Riverside, Conn.

[73] Assignee: USV Pharmaceutical Corporation, Tarrytown, N.Y.

[21] Appl. No.: 471,593

[22] Filed: Mar. 3, 1983

[51] Int. Cl.³ .................. A61K 31/535; C07D 413/06
[52] U.S. Cl. .................... 514/228; 544/122; 544/128; 544/131; 514/232; 514/233; 514/236
[58] Field of Search ............ 544/122, 128, 131; 424/248.5, 248.51, 248.52, 248.54, 248.55

[56] References Cited

U.S. PATENT DOCUMENTS 4,258,042  3/1981  Loev et al. .................... 544/131

Primary Examiner—Robert W. Ramsuer

[57] ABSTRACT

The compounds of the formula:

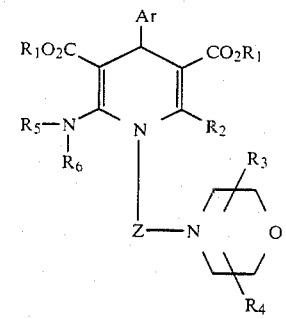

wherein each of the substituents is as defined herein are useful anti-hypertensive agents.

23 Claims, No Drawings

N-SUBSTITUTED 1,4-DIHYDROPYRIDINES AND PHARMACEUTICAL COMPOSITIONS

This invention relates to new anti-hypertensive agents and more particularly to certain new substituted 1,4-dihydropyridines possessing useful anti-hypertensive activity.

Substituted 1,4-dihydropyridines are known and have been described in the literature as vasodilating agents. 1,4-Dihydropyridines having vasodilating activity are characterized by the presence of alkyl substituents in the 2 and 6 positions of the pyridine ring and carbalkoxy groups in the 3,5-positions usually with a substituent, most commonly phenyl or substituted phenyl, in the 4-position. To increase the water-solubility of these compounds, M. Iwanami, et al. [Chem. Pharm. Bull. 27 (6), 1426-1440 (1979)] described the effect of N-substitution of the pyridine ring nitrogen with, inter alia, aminoalkylene groups such as pyrrolidinoethyl and dimethylaminoethyl. Thus, water-solubility determinations with compounds such as diethyl 1,4-dihydro-4-(3-nitrophenyl)-2,6-dimethyl-1-(2-pyrrolidinoethyl)-3,5-pyridinedicarboxylate and the corresponding 1-(2-dimethylaminoethyl) compound were determined as was the potency thereof as vasodilators but these compounds were determined to be of lower potency than known compounds such as the corresponding 1-ethoxymethyl compound.

Japanese specification No. 70767/76 describes as anti-hypertensive and vasodilating agents 1,4-dihydropyridines of the formula

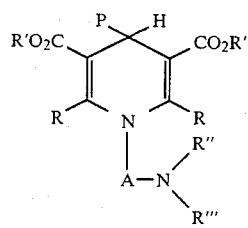

in which R is alkyl; P is substituted (mono or di-) phenyl, pyridyl, furyl, or thienyl in which the substituents are H, halogen, —CN, NO$_2$, —NH$_2$, —N(CH$_3$)$_2$, carboxyl, methoxy, ethoxy, butoxy, sulfonyl, methylsulfonyl or acetyl; R' is alkyl, aralkyl, methyl, ethyl, isopropyl, t-butyl, ethoxyethyl, benzyl, phenethyl, or 4-methoxybenzyl; A is alkylene; and R" and R''' are each alkyl and, when taken together, form a pyrrolidine ring with the N to which they are attached.

U.S. Pat. No. 4,258,042 describes N-morpholinodihydropyridines of the formula:

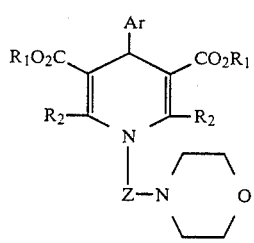

wherein Ar is heteroaryl, cycloalkyl or

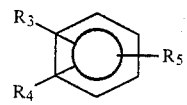

wherein each of $R_3$, $R_4$ and $R_5$ is H, alkyl, aryl, halo, lower alkoxy, nitro, amino, alkylmercapto, cyano, carboxy, carbalkoxy, sulfamyl, trifluoromethyl, hydroxy, acyloxy, methanesulfonyl, alkylamino or acylamino; and $R_3$ and $R_4$, when taken together, form a methylenedioxy; Z is alkylene containing 1 to about 5 carbon atoms in the principal chain; and each $R_1$ and $R_2$ is alkyl; and acid addition salts thereof.

The new compounds of the present invention are N-substituted dihydropyridines of the formula:

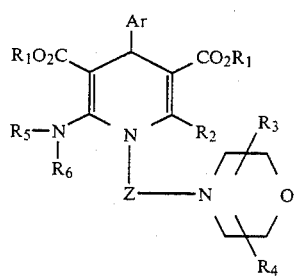

FORMULA I wherein Ar is heteroaryl, cycloalkyl or

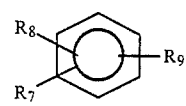

wherein each of $R_7$, $R_8$ and $R_9$ is H, alkyl, aryl, halo, lower alkoxy, nitro, amino, alkylmercapto, cyano, carboxy, carbalkoxy, sulfamyl, trifluoromethyl, hydroxy, acyloxy, methanesulfonyl, alkylamino or acylamino; and $R_7$ and $R_8$, when taken together, form a methylenedioxy; Z is alkylene containing 1 to about 5 carbon atoms in the principal chain; $R_3$ and $R_4$ are each H or alkyl; and each $R_1$, $R_2$ $R_5$ and $R_6$ is alkyl; and acid addition salts thereof.

The total number of carbon atoms in each such hydrocarbyl substituent can range up to about 10. The substituent "Z" contains up to about 5 carbons in the principal chain, i.e. the straight chain of carbons between the terminal valences, but can be branched in that methyl and ethyl substituents can be present on the principal chain. Thus, the alkylene chain Z can contain a total number of carbon atoms greater than 5, preferably no more than about 8.

Heteroaryl as employed herein refers to any heterocyclic structure in which at least one of O, S and N are present as the hetero atoms. These include thiophene, furan, pyridine, thiazole, pyrimidine, pyrrole, benzofuran, quinoline, benzothiophene and substituted heterocycles.

The preferred compounds are those in which the hydrocarbyl radicals contain up to about 7 carbon atoms when aliphatic and up to about 10 carbon atoms when aromatic, e.g., phenyl, tolyl and naphthyl.

The particularly preferred compounds of the invention are those in which Z is —CH$_2$CH$_2$— and Ar is a nitrophenyl or a trifluoromethylphenyl group, especially 2-trifluoromethylphenyl or 2-nitrophenyl.

The new compounds of the invention can be prepared by art-recognized procedures from known starting compounds as described, for example, in the literature hereinbefore described. The following procedure constitutes a particularly convenient preparative method:

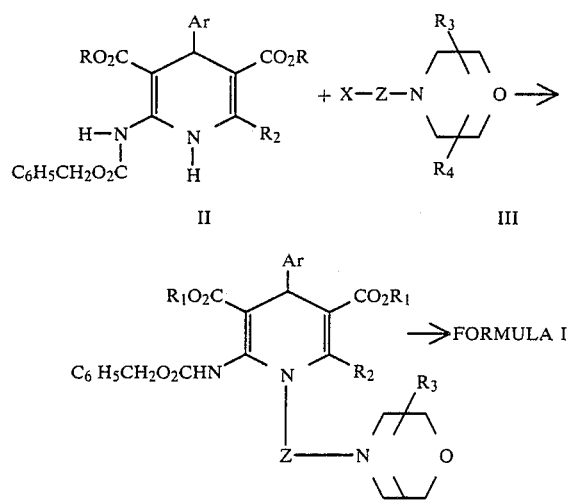

The reaction can be carried out in a solvent in the presence of sodium hydride, or any alkali metal hydride or alkoxide as is commonly employed in condensation reactions. The reaction is effected in two steps, the first, metallation with the alkali metal compound, and the second, condensation with the halide "X", containing compound, which is usually chloride. The hydrides are convenient since the progress of the metallation reaction can be followed by observing the evolution of hydrogen gas. The metallation step is normally carried out at room temperatures. The reaction mixture thereafter is heated at elevated temperature, e.g. at steam bath temperature at or about 100° C., or above up to about 150° C. depending on the boiling point of the selected solvent, and the halide compound is then added, usually in controlled amounts in dropwise fashion and, after addition is completed, the reaction mixture is heated at the elevated temperature.

The product is then obtained in the usual fashion, as by cooling to cause precipitation or evaporation of the solvent to obtain the product as a residue, followed by hydrogenalysis and alkylation to obtain the desired compounds.

The present new compounds can also be prepared by direct alkylation of the corresponding compounds in which $R_5$ and $R_6$ are hydrogen, either in stepwise fashion forming first the monoalkylated compound and then the dialkylated compound, or in batch reaction using two equivalents of alkylating agent for each equivalent of starting unsubstituted-amino compound.

The compounds in which $R_5$ and $R_6$ are each hydrogen are also new products useful as intermediates for production of the final therapeutic compounds of this invention. They are prepared by condensation of the corresponding 2-amino-dihydropyridine (compounds of Formula II herein, wherein $R_5$ and $R_6$ are each hydrogen) with the morpholine compound of formula III herein. Preferably, the 2-amino group is blocked to prevent secondary reaction with the halide compound of formula II, e.g., with an acyl blocking groups such as a lower alkanoyl groups or a carbobenzyloxy groups or other blocking group employed for the same purpose. The blocking group can be removed after condensation by hydrolysis in the case of alkanoyl blocking groups or by hydrogenolysis remove the carbobenzyloxy group.

The aforesaid alkylation procedure can be effected employing usual amine-alkylating agents such as alkyl halides and dialkyl sulfates, e.g., dimethyl sulfate, ethyl iodide, methyl bromide and methyl iodide, preferably in the presence of a base, such as a hydrogen halide acceptor.

The present new compounds have a chiral center at the carbon to which the Ar group is attached and therefore exist in stereoisomeric forms, i.e., in the "S" and "R" forms. The desired "S" form can be separated from the "R" form by known methods of resolution, e.g., by chromatographic techniques. Of course, mixtures of the isomers can be used for therapeutic purposes without resolution.

Employing these procedures, a variety of new N-morpholinoalkyl 1,4-dihydropyridines of the following formula can be prepared:

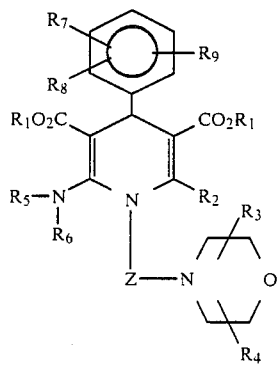

| Z | $R_2$ | $R_1$ | $R_5 + R_6$ | $R_9$ at 4 position | $R_8$ at 3 position | $R_7$ at 2 position |
|---|---|---|---|---|---|---|
| $CHCH_3$ | $CH_3$ | $C_2H_5$ | $CH_3$ | H | H | H |
| $CHCH_3$ | $CH_3$ | $C_2H_5$ | $C_2H_5$ | H | $CH_3$ | H |
| $CH_2CH_2$ | $CH_3$ | $C_2H_5$ | $CH_3$ | H | H | H |

-continued

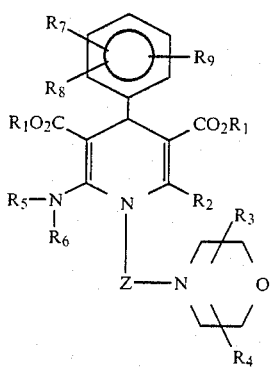

| Z | $R_2$ | $R_1$ | $R_5 + R_6$ | $R_9$ at 4 position | $R_8$ at 3 position | $R_7$ at 2 position |
|---|---|---|---|---|---|---|
| $CH(CH_3)CH_2$ | $C_2H_5$ | $C_2H_5$ | $CH_3$ | H | H | Cl |
| $CH_2CH_2$ | $CH_3$ | $i-C_3H_7$ | $CH_3$ | H | CN | H |
| $CH_2CH_2$ | $CH_3$ | $C_2H_5$ | $CH_3$ | H | H | $NO_2$ |
| $CH_2CH_2$ | $CH_3$ | $C_2H_5$ | $C_2H_5$ | H | OH | H |
| $CH_2CH_2$ | $C_3H_7$ | $CH_3$ | $C_3H_7$ | H | H | $CF_3$ |
| $CH(CH_3)$ | $C_4H_9$ | $C_2H_5$ | $C_2H_5$ | H | $OCH_3$ | H |
| $(CH_2)_3$ | $C_6H_{13}$ | $C_2H_5$ | $CH_3$ | H | $COOH_3$ | H |
| $CH_2CH_2$ | $i-C_4H_9$ | $CH_3$ | $CH_3$ | $OCH_3$ | H | H |
| $CH_2CH_2$ | $CH_3$ | $C_2H_5$ | $CH_3$ | H | $OCH_3$ | $OCH_3$ |
| $(CH_2)_5$ | $CH_3$ | $C_2H_5$ | $CH_3$ | H | $CH_3$ | $CH_3$ |
| $CH_2CH_2$ | $CH_3$ | $C_2H_5$ | $CH_3$ | H | H | $CH_2C_6H_5$ |
| $CH_2CH_2$ | $CH_3$ | $C_2H_5$ | $CH_3$ | H | H | $C(CH_3)_3$ |
| $CH(CH_3)CH_2$ | $CH_3$ | $C_2H_5$ | $CH_3$ | H | H | $C_6H_5$ |
| $CH_2CH_2$ | $CH_3$ | $C_2H_5$ | $CH_3$ | H | H | H |
| $CH_2CH_2$ | $CH_3$ | $C_2H_5$ | $CH_3$ | Cl | Cl | Cl |
| $CH_2CH_2$ | $CH_3$ | $C_2H_5$ | $CH_3$ | Cl | H | Cl |
| $CH_2CH_2$ | $CH_3$ | $C_2H_5$ | $CH_3$ | Cl | H | Cl |
| $CH_2CH_2$ | $CH_3$ | $C_2H_5$ | $CH_3$ | $OCH_3$ | H | $CH_2=CH-CH_2$ |
| $CH_2CH_2$ | $CH_3$ | $C_2H_5$ | $CH_3$ | H | H | H |
| $CH_2CH_2$ | $CH_3$ | $C_2H_5$ | $CH_3$ | H | $CH_3$ | H |
| $CH_2CH_2$ | $CH_3$ | $C_2H_5$ | $CH_3$ | H | H | H |
| $CH_2CH_2$ | $CH_3$ | $C_2H_5$ | $CH_3$ | H | $CH_3$ | H |
| $CH_2CH_2$ | $CH_3$ | $C_2H_5$ | $CH_3$ | H | $CH_3$ | $CH_3$ |
| $CH_2CH_2$ | $CH_3$ | $C_2H_5$ | $CH_3$ | H | H | H |
| $CH_2CH_2$ | $CH_3$ | $C_2H_5$ | $CH_3$ | H | $CH_3$ | H |
| $CH_2CH_2$ | $CH_3$ | $C_2H_5$ | $CH_3$ | H | H | Cl |
| $CH_2CH_2$ | $CH_3$ | $C_2H_5$ | $CH_3$ | H | CN | H |
| $CH_2CH_2$ | $CH_3$ | $C_2H_5$ | $CH_3$ | $NO_2$ | H | H |
| $CH_2CH_2$ | $CH_3$ | $C_2H_5$ | $CH_3$ | H | OH | H |
| $CH_2CH_2$ | $CH_3$ | $C_2H_5$ | $CH_3$ | H | $CF_3$ | H |
| $CH_2CH_2$ | $CH_3$ | $C_2H_5$ | $CH_3$ | H | $OCH_3$ | H |
| $CH_2CH_2$ | $CH_3$ | $C_2H_5$ | $CH_3$ | H | COOH | H |
| $CH_2CH_2$ | $CH_3$ | $C_2H_5$ | $CH_3$ | $OCH_3$ | H | H |
| $CH_2CH_2$ | $CH_3$ | $C_2H_5$ | $CH_3$ | H | $OCH_3$ | $OCH_3$ |
| $CH_2CH_2$ | $CH_3$ | $C_2H_5$ | $CH_3$ | H | H | $OCH_3$ |
| $CH_2CH_2$ | $CH_3$ | $C_2H_5$ | $CH_3$ | $OCH_3$ | H | $CH_2=CH-CH_2-$ |
| $CH_2CH_2$ | $CH_3$ | $C_2H_5$ | $CH_3$ | H | H | $COOCH_3$ |
| $CH_2CH_2$ | $CH_3$ | $C_2H_5$ | $CH_3$ | $OCH_3$ | H | $COOCH_3$ |
| $CH_2CH_2$ | $CH_3$ | $C_2H_5$ | $CH_3$ | H | H | $-(CH_2)_4-$ |
| $CH_2CH_2$ | $CH_3$ | $C_2H_5$ | $CH_3$ | H | H | $NH_2$ |

Compounds wherein $R_5$ and $R_6$ are different can also be prepared by selection of suitable 2-amino dihydropyridine compounds of Formula II herein.

Corresponding compounds wherein the morpholine moiety is substituted by lower alkyl groups can also be prepared by substitution of the corresponding alkylmorpholine starting compound.

The compounds of this invention are characterized by high anti-hypertensive activity with little, if any, adverse side effects.

The present new heterocyclic compounds are therapeutically useful as such or can be employed in the form of salts in view of their basic nature. Thus, these compounds form salts with a wide variety of acids, inorganic and organic, including therapeutically-acceptable acids. The salts with therapeutically-acceptable acids are, of course, useful in the preparation of formulations where water solubility is desired. The salts with therapeutically-unacceptable acids are particularly useful in the isolation and purification of the present new compounds. Therefore, all acid salts of the present new compounds are contemplated by the present invention.

The pharmaceutically-accepted acid addition salts are of particular value in therapy. These include salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycolic, gluconic, succinic, arylsulfonic, e.g. p-toluenesulfonic acids, and the like. The pharmaceutically-unacceptable acid addition salts, while not useful for therapy, are valuable for isolation and purification of the new substances. Further, they are useful for the preparation of pharmaceutically-acceptable salts. Of this group, the more common salts include those formed with hydrofluoric and perchloric acids. Hydrofluoride salts are particularly useful for the preparation of the pharmaceutically-acceptable salts, e.g., the hydrochlorides, by solution in hydrochloric acid and crystallization of the hydrochloride salt formed. The perchloric acid salts are useful for purification and crystallization of the new products.

As therapeutic agents, the present new heterocyclic compounds are particularly useful as anti-hypertensive agents. The therapeutic agents of this invention may be administered alone or in combination with pharmaceutically-acceptable carriers, the proportion of which is determined by the solubility and chemical nature of the compound, chosen route of administration and standard pharmaceutical practice. For example, they may be administered orally in the form of tablets or capsules containing such excipients as starch, milk sugar, certain types of clay and so forth. They may be administered orally in the form of solutions which may contain coloring and flavoring agents or they may be injected parenterally, that is, intramuscularly, intravenously or subcutaneously. For parenteral administration, they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as other anti-hypertensive agents and the dosage level is of the same order of magnitude as is generally employed with these other therapeutic agents. The therapeutic dosage will generally be from 10 to 750 milligrams per day and higher, although it may be administered in several different dosage units. Tablets containing from 10 to 250 mg. of active agent are particularly useful.

The following examples further illustrate the invention.

EXAMPLE I

Diethyl 1,4-dihydro-4-(2-trifluoromethylphenyl)-2-Dimethylamino-6-methyl-1-(2-morpholinoethyl)-3,5-pyridine dicarboxylate The starting 2-carbobenzyloxyamino compound is prepared by condensation of ethyl 2-(o-trifluoromethylbenzylidine)-3-oxobutanoate, and ethyl 3-diamino acrylate in pyridine in the presence of pyridine hydrochloride followed by reaction of the product with equivalent of potassium carbonate dimethylformamide (DMF).

To a suspension of sodium hydride (50% suspension in mineral oil) in 100 ml of dry distilled DMF is added a solution of diethyl 1,4-dihydro-4-(2-trifluoromethylphenyl)-2-carbobenzyloxyamino-6-methyl-3,5-pyridine dicarboxylate (0.1 mole) in 150 ml of DMF. After the gassing has ceased, to the hot solution is added quickly a toluene solution of 2-chloroethylmorpholine (0.1 mole). The reaction mixture is heated at 100°–110° C. for a period of 8 hours and then cooled. The unreacted NaH and NaCl is filtered off and the solvent removed from the filtrate. The residue is hydrogenated over 10% Pd/C in a Parr apparatus to obtain the 2-amino product which is recrystallized from hexane.

Methylation with 2 equivalents of methyl iodide gives the final product.

EXAMPLE II

Diethyl 1,4-dihydro-4-(2-nitrophenyl)-2-dimethylamino-6-methyl-1-(2-morpholinoethyl)-3,5-pyridine dicarboxylate To a suspension of sodium hydride (50% suspension in mineral oil) in 100 ml of dry distilled DMF is added a solution of diethyl 1,4-dihydro-4-(2-nitrophenyl)-2-carbobenzyloxyamino-6-methyl-3,5-pyridine dicarboxylate (0.1 mole) in 150 ml of DMF. After the gassing ceases, to the hot solution is added quickly a toluene solution of 2-chloroethylmorpholine (0.1 mole). The reaction mixture is heated at 100°–110° C. for a period of 8 hours and then cooled. The unreacted NaH and NaCl is filtered off and the solvent removed from the filtrate. The residue is hydrogenated over 10% Pd/C in a Parr apparatus to obtain the 2-amino product which is recrystallized from hexane.

Methylation with 2 equivalents of methyl iodide gives the final product.

What is claimed is:

1. A compound of the formula:

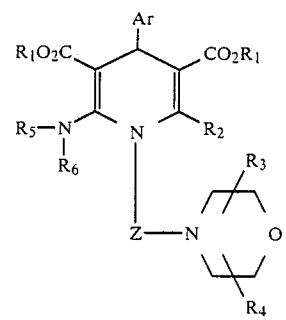

wherein Ar is heteroaryl, cycloalkyl or

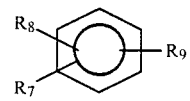

wherein each of $R_7$, $R_8$ and $R_9$ is H, alkyl, aryl, halo, lower alkoxy, nitro, amino, alkylmercapto, cyano, carboxy, carbalkoxy, sulfamyl, trifluoromethyl, hydroxy, acyloxy, methanesulfonyl, alkylamino or acylamino; and $R_7$ and $R_8$, when taken together, form a methylenedioxy; Z is alkylene containing 1 to about 5 carbon atoms in the principal chain; $R_3$ and $R_4$ are each H or alkyl; and each $R_1$, $R_2$, $R_5$ and $R_6$ is alkyl; and acid addition salts thereof.

2. The compound according to claim 1 wherein Ar is a monosubstituted phenyl group and Z is —CH$_2$—CH$_2$—.

3. The compound according to claim 1 wherein heteroaryl is thienyl, furyl, thiazolyl, pyridyl or quinolinyl.

4. The compound according to claim 1 wherein Ar is a trifluoromethylphenyl.

5. The compound according to claim 1 wherein Ar is a trifluoromethylphenyl and Z is —CH$_2$—CH$_2$—.

6. Diethyl 1,4-dihydro-4-(2-trifluoromethylphenyl)-2-dimethylamino-6-methyl-1-(2-morpholinoethyl)-3,5-pyridine dicarboxylate.

7. A pharmaceutically-acceptable acid addition salt of the compound of claim 6.

8. An anti-hypertensive composition comprising a compound according to claim 1 and pharmaceutically acceptable carrier.

9. An anti-hypertensive compound of the formula

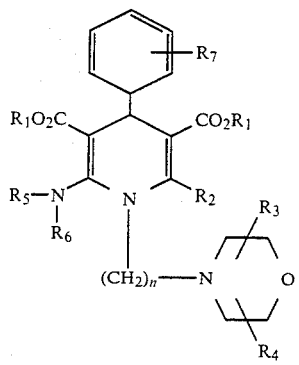

wherein $R_1$ and $R_2$ are each lower alkyl, n is the integer 2, 3 or 4, $R_3$ and $R_4$ are each hydrogen or alkyl, $R_7$ is H, trifluoromethyl, methoxy, or nitro, and $R_5$ and $R_6$ are each alkyl, and pharmaceutically-acceptable salts thereof.

10. The compound according to claim 9 wherein $R_7$ is trifluoromethyl.

11. The compound according to claim 9 wherein $R_7$ is nitro.

12. The compound according to claim 9 wherein n is 2.

13. An antihypertensive compound of the formula

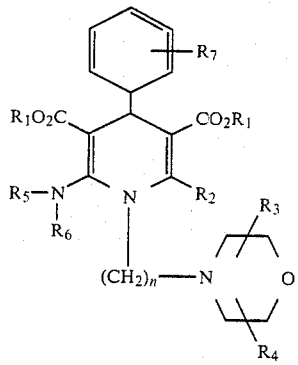

wherein $R_1$, $R_2$, $R_5$ and $R_6$ are each lower alkyl and $R_7$ is H, trifluoromethyl, methoxy, or nitro, and pharmaceutically-acceptable salts thereof.

14. The compound according to claim 13 wherein $R_7$ is trifluoromethyl.

15. The compound according to claim 13 wherein $R_7$ is nitro.

16. The compound according to claim 13 wherein $R_7$ is methoxy.

17. The compound according to claim 14 wherein each $R_1$ is methyl or ethyl and $R_2$ is methyl.

18. The compound according to claim 15 wherein each $R_1$ is methyl or ethyl and $R_2$ is methyl.

19. The compound according to claim 16 wherein each $R_1$ is methyl or ethyl and $R_2$ is methyl.

20. A pharmaceutically-acceptable salt of the compound according to claim 17.

21. A pharmaceutically-acceptable salt of the compound according to claim 18.

22. A pharmaceutically-acceptable salt of the compound according to claim 19.

23. An antihypertensive composition comprising a compound according to claim 1 and pharmaceutically acceptable carrier.

* * * * *